United States Patent  
Danko

(10) Patent No.: US 6,879,391 B1
(45) Date of Patent: Apr. 12, 2005

(54) PARTICLE DETECTION METHOD AND APPARATUS

(75) Inventor: Joseph J. Danko, Shrewsbury, MA (US)

(73) Assignee: KLA-Tencor Technologies, Milpitas, CA (US)

( * ) Notice: Subject to any disclaimer, the term of this patent is extended or adjusted under 35 U.S.C. 154(b) by 0 days.

(21) Appl. No.: 09/579,620

(22) Filed: May 26, 2000

Related U.S. Application Data

(60) Provisional application No. 60/135,956, filed on May 26, 1999.

(51) Int. Cl.[7] .............................................. G01N 21/88
(52) U.S. Cl. .................................................. 356/237.4
(58) Field of Search ........................... 356/237.4, 237.5

(56) References Cited

U.S. PATENT DOCUMENTS

| | | |
|---|---|---|
| 4,377,340 A | 3/1983 | Green et al. |
| 4,806,744 A | 2/1989 | Briane et al. |
| 4,895,446 A | 1/1990 | Maldari et al. |
| 4,898,471 A | 2/1990 | Vaught et al. |
| 5,046,847 A | 9/1991 | Nakata et al. |
| 5,317,380 A | 5/1994 | Allemand |
| 5,617,203 A * | 4/1997 | Kobayashi et al. ...... 358/237.5 |
| 5,659,390 A * | 8/1997 | Danko ....................... 356/237.4 |
| 5,748,266 A * | 5/1998 | Kodate ........................ 349/39 |
| 5,805,278 A | 9/1998 | Danko |

\* cited by examiner

Primary Examiner—Richard A. Rosenberger
(74) Attorney, Agent, or Firm—Ann Marie Mewherter; Daffer McDaniel, LLP

(57) ABSTRACT

An apparatus and method for detecting pattern defects and/or particles on the front surface of a semiconductor wafer having repetitive patterns includes a laser for illuminating an area on the front surface with a beam of polarized light. A lens collects light scattered from the area and forms a Fourier diffraction pattern of the area illuminated. A Fourier mask blocks out scattered light collected by the lens at locations in the Fourier diffraction pattern where the intensity is above a predetermined level indicative of background information and leaves in light at locations where the intensity is below the threshold level indicative of possible particle information. The Fourier mask includes a spatial light modulator and a polarization discriminator. The lens also images the area illuminated onto a camera using scattered light collected from the area by the lens and not blocked out by the Fourier mask. In one embodiment of the invention the spatial light modulator is optically addressable and in other embodiments of the invention the spatial light modulator is electrically addressable.

2 Claims, 7 Drawing Sheets

PARTICLE DETECTION METHOD AND APPARATUS

This application claims the priority of Provisional application Ser. No. 60/135,956 filed on May 26, 1999 in the name of Joseph J. Danko.

BACKGROUND OF THE INVENTION

The present invention relates generally to a method and apparatus for detecting the presence of particles on the surface of an object and more particularly to a method and apparatus for detecting contaminant particles on a surface of a semiconductor wafer using the principle of light scattering, the surface having repetitive patterns. An example of a semiconductor wafer having a surface containing repetitive patterns is a memory wafer.

There are a variety of existing ways for detecting and measuring the number and sizes of particles on the surface of a semiconductor wafer for the purpose of rejecting those wafers which have on their surface one or more particles above certain sizes or an excessive number of particles. One of the more simple methods involves having a human operator inspect the wafer using a light field/dark field microscope. Using the eye, the operator actually counts the number of particles and also identifies the size of the particles, such as those between 1 and 20 microns, and then rejects those wafers which have particles of or above a certain size or which have an excessive number of particles. This method, however, is highly inaccurate and very expensive both in terms of wages for the human operator and in terms of the number of rejects both after the inspection and after production of the chips (when an erroneously passed wafer is found to have an electrical defect, e.g. short circuits, because of the presence of contaminant particles).

In U.S. Pat. No. 5,805,278, issued on Sep. 8, 1998 to Joseph J. Danko and assigned to Inspex, Inc., which patent is incorporated herein by reference, there is disclosed an apparatus and method for detecting particles on a surface of a semiconductor wafer having repetitive patterns which includes a laser for illuminating an area on the front surface at grazing angle of incidence with a beam of polarized light. A lens collects light scattered from the area and forms a Fourier diffraction pattern of the area illuminated. A Fourier mask blocks out light collected by the lens at locations in the Fourier diffraction pattern where the intensity is above a predetermined level indicative of background information and leaves in light at locations where the intensity is below the threshold level indicative of possible particle information. The Fourier mask includes an optically addressable spatial light modulator and a polarization discriminator. Several embodiments of the invention are described. In some embodiments, the polarization discriminator is in the form of a crossed polarizer while in other embodiments the polarization discriminator is in the form of a polarizing beamsplitter. A camera detects scattered light collected from the area by the lens and not blocked out by the Fourier mask.

In U.S. Pat. No. 5,317,380, issued May 31, 1994, and assigned to Inspex, Inc. there is disclosed a method and apparatus for detecting particles on a surface of an object, such as a virgin or patterned semiconductor wafer, ceramic tile, or the like. In one embodiment, an apparatus is provided in which a scanning beam of laser light is brought to focus as an arcuate scan line on a surface of the object at a grazing angle of incidence using an off-axis hypertelecentric mirror. A pair of light detectors are positioned at a meridional angle of about 30 degrees and at an azimuthal angle of about 4 degrees to measure forward scattered light form the surface. The object is then moved translationally so that the beam can scan another line of the surface. A light trap is provided to trap light that is reflected by the surface, and a series of masks are provided to mask light which is scattered by the hypertelecentric mirror and in the case of pattered objects, light which is diffracted by the pattern imprinted on the object.

In U.S. Pat. No. 5,046,847, issued on Sep. 10, 1991 and assigned to Hitachi Ltd. there is disclosed a method and apparatus for detecting foreign matter on a sample by illuminating a stripe-shaped region with linearly polarized light. Some of the light reflected by the sample is intercepted by a light intercepting state, and the rest of the light reflected by, the sample, which passes through the light intercepting stage is directed to a detecting optical system, to be detected by a photodetector. The sample is illuminated obliquely at a predetermined angle with respect to a group of straight lines constituting a primary pattern on the sample. The angle is selected so that the diffraction light reflected by the group of straight lines does not enter the detecting optical system. A polarizing spatial filter using a liquid crystal element may be disposed in a predetermined restricted region, in a spacial frequency region, or Fourier transformation plane, within the detecting optical system. The light scattered by the sample may further be separated in the detecting optical system into partial beams having different wave orientation characteristics, which characteristics are detected by a number of one-dimensional solid state imaging elements. The signals are processed by a driver, adder, and quantizer in synchronism with the one-dimensional solid state imaging elements.

In U.S. Pat. No. 4,898,471, issued Feb. 6, 1990, and assigned to Tencor Instruments, a system for detecting particles and other defects on a patterned semiconductor wafer, photomask, or the like is disclosed. The system includes a light source for emitting a beam of light. A polarizing filter is used to polarize the beam of light in a direction substantially parallel to the surface of the patterned semiconductor wafer to be examined. The beam is enlarged in cross-sectional diameter by a beam expander placed along the path of the beam after the polarizing filter. The beam is then caused to scan by a deflection mirror. A telecentric lens brings the scanning beam to focus on the patterned wafer at a shallow angle of incidence, the beam striking the wafer surface substantially parallel to the pattern streets formed on the wafer. A light collection system for detecting side scattered light is positioned in the plane of the scan line. The light collection system, which includes a lens for focusing the side scattered light, a polarizing filter oriented in a direction substantially parallel to the surface of the patterned wafer, and a photomultiplier tube for detecting light incident thereon and transmitting electrical signals in response thereto, receives light scattered in a direction less than 15 degrees above the surface and a angel relative to the beam direction in a range from about 80 degrees to 100 degrees. A processor constructs templates from the electrical signal corresponding to individual patterns and compares the templates to identify particles.

In U.S. Pat. No. 4,806,744 issued Feb. 21, 1989 and assigned to Insystems, Inc., there is disclosed an inspection system which employs a Fourier transform lens and an inverse Fourier transform lens positioned along an optic axis to produce from an illuminated area of a patterned specimen wafer a spatial frequency spectrum whose frequency components can be selectively filtered to produce an image pattern of defects in the illuminated are of the wafer.

Depending on the optical components configuration of the inspection system, the filtering can be accomplished by a spatial filter of either the transmissive or reflective type. The lenses collect light diffracted by a wafer die aligned with the optic axis and light diffracted by other wafer dies proximately located to such die. The inspection system is useful for inspecting only dies having many redundant circuit patterns. The filtered image strikes the surface of a two-dimensional photodetector array which detects the presence of light corresponding to defects in only the illuminated on-axis wafer die. Inspection of all possible defects in the portions of the wafer surface having many redundant circuit patterns is accomplished by mounting the wafer onto a two-dimensional translation stage and moving the stage so that the illuminated area continuously scans across the wafer surface from die to die until the desired portions of the wafer surface have been illuminated. The use of a time delay integration technique permits continuous stage movement and inspection of the wafer surface in a raster scan fashion.

In U.S. Pat. No. 4,895,446 to M. C. Maldari et al., there is disclosed a method and apparatus for detecting the presence of particles on the surface of an object such as the front side of a patterned semiconductor wafer. A vertically expanded, horizontally scanning, beam of light is directed onto an area on the surface of the object at grazing angle of incidence. A video camera positioned above the surface detects light scattered from any particles which may be present on the surface, but not specularly reflected light. The surface is angularly repositioned (rotated) relative to the incident light beam so that the diffracted light form the surface and the pattern of lines on the surface is at a minimum. The object is then moved translationally to expose another area to the incident light beam so that the entire surface of the object or selected portions thereof can be examined, one area at a time. The patent also discloses the use of a mask containing a pattern corresponding to the Fourier transform of the patterned surface to mask off light scattered form the pattern on the surface but not any particles that may be present on the surface.

In U.S. Pat. No. 4,377,340 to G. P. Green et al., and assigned to Hamamatsu Systems, Inc., there is disclosed a method and apparatus for detecting and measuring the number and sizes of impurities on the surface of a material, such as a semiconductor wafer, wherein a beam of high intensity collimated light from a xenon arc lamp is directed onto the surface at normal incidence in the absence of any extraneous light, through a collimating mirror and a pin hole device and whereat the particles will scatter the light, and wherein the surface is viewed by a high light sensitive TV camera which is positioned off-axis to pick up scattered light but not specularly reflected light for display on a viewing screen.

Another reference of interest is U.S. Pat. No. 5,659,390 issued on Aug. 19, 1997 in the name of Joseph J. Danko, and is assigned to Inspex, Inc. which patent is incorporated herein by reference.

SUMMARY OF THE INVENTION

It is an object of the present invention to provide a new and improved method and apparatus for detecting the presence of pattern defects and/or contaminant particles on a surface of a semiconductor wafer using the principle of scattered light, the surface having repetitive patterns.

It is another object of the present invention to provide a method and apparatus as described above in which background scatter is filtered out in a new and novel manner.

It is a further object of the present invention to provide a method and apparatus as described above which is designed for use in dark field and bright field illumination applications.

Other objects, as well as features and advantages of the present invention, will be set forth in part in the description which follows, and in part will be obvious from the description or may be learned by practice of the invention. The objects, features and advantages of the invention may be realized and attained by means of the instrumentalities and combinations particularly pointed out in the appended claims.

Apparatus for detecting pattern defects and/or contaminant particles on a surface of a semiconductor wafer having repetitive patterns according to this invention comprises a laser for illuminating an area on said surface with a beam of polarized light, an imaging lens for collecting light scattered from the area illuminated, the imaging lens forming a Fourier diffraction pattern of the scattered light from the area illuminated, a Fourier mask for blocking out from the scattered light collected by the imaging lens areas in the Fourier diffraction pattern whose intensity is above a predetermined level indicative of background information and letting pass through areas in the Fourier diffraction pattern whose intensity is below the threshold level indicative of possible particle information, the Fourier mask being programmable and including a spatial light modulator (SLM) and a polarization discriminator, and a camera for receiving an image of the area imaged by the imaging lens using scattered light collected by imaging lens and not blocked out by the Fourier mask. In one embodiment of the invention, the spatial light modulator is optically addressable and in other embodiments of the invention, the spatial light modulator is electrically addressable.

A method for detecting contaminant particles and/or pattern defects on the front surface of a patterned semiconductor wafer having repetitive pattern according to this invention comprises illuminating an area on the front surface with a beam of polarized light, collecting light scattered from the area illuminated and forming a Fourier diffraction pattern of the light scattered from the area illuminated, blocking out from the light collected areas in the Fourier diffraction pattern whose intensity is above a predetermined level indicative of background information and letting pass through areas in the Fourier diffraction pattern whose intensity is below the threshold level indicative of possible particle information, the blocking being achieved using a mask including a spatial light modulator, and a polarization discriminator, and imaging area illuminated onto a camera using scattered light not blocked out.

BRIEF DESCRIPTION OF THE DRAWINGS

In the drawings wherein like reference numerals represent like parts.

DETAILED DESCRIPTION OF PREFERRED EMBODIMENTS

The present invention is directed to a method and apparatus for detecting the presence of contaminant particles and/or pattern defects on the surface of a semiconductor wafer using the principle of scattered light, the surface having repetitive patterns.

In accordance with the invention, an area on the surface to be examined is illuminated with a beam of polarized light. An imaging lens collects light scattered from the area illuminated, the imaging lens forming in its back focal plane a Fourier diffraction pattern of the scattered light. A Fourier mask blocks out light in areas in the Fourier diffraction pattern above a predetermined intensity level, indicative of background information of the wafer and does not block out light in areas which is below the predetermined intensity level, indicative of possible particles and/or pattern defects. The area illuminated is then imaged onto a camera using scattered light not blocked out by the Fourier mask. The procedure is repeated for other areas on the surface.

The Fourier mask is programmable and includes a spatial light modulator (SLM) and a polarization discriminator. In one embodiment of the invention the SLM is optically addressable, while in other embodiments of the invention the SLM is electrically addressable.

Figure 1:
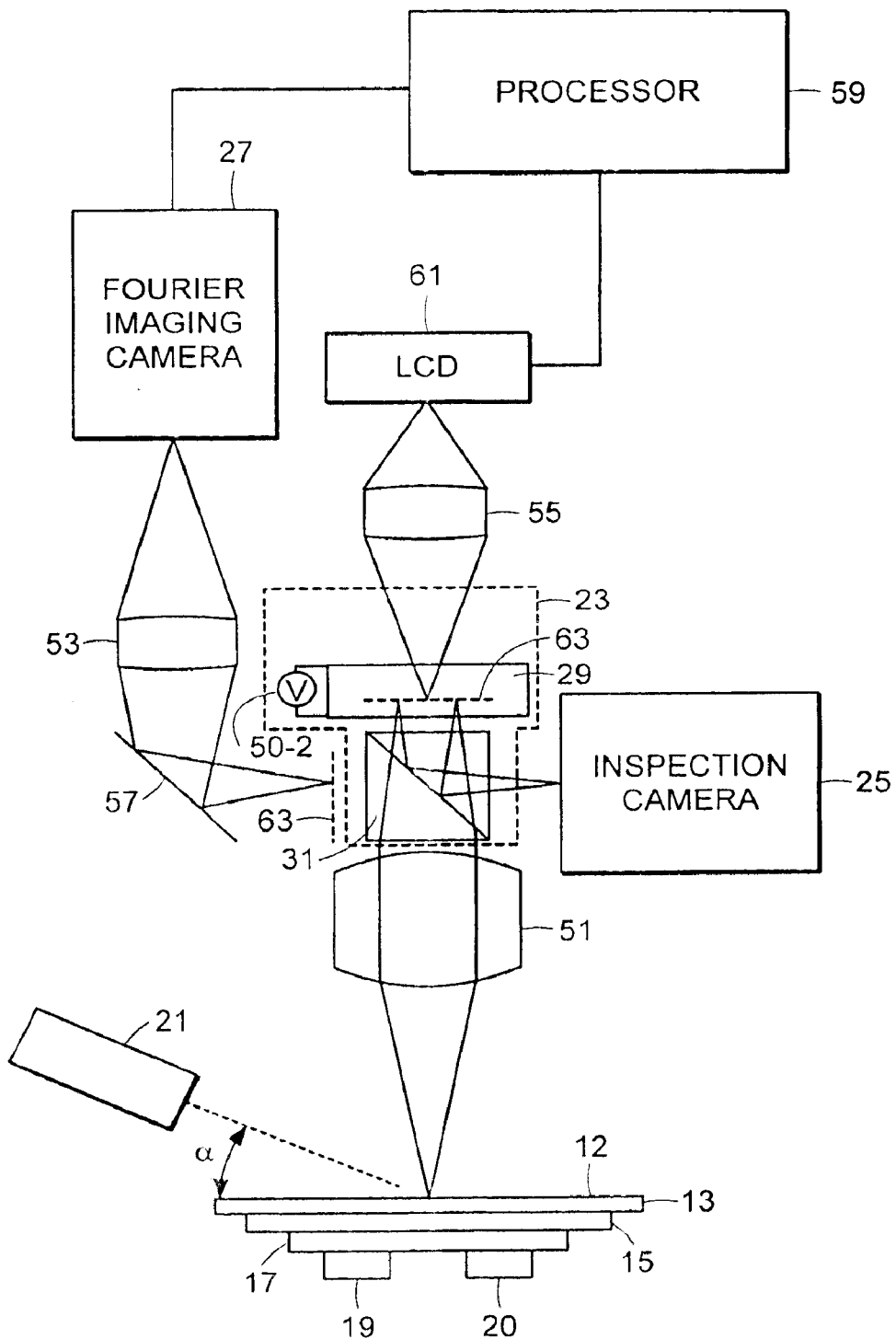
FIG. 1 is a schematic representation of an embodiment of an apparatus constructed according to the teaching of the present invention for detecting the presence of contaminant particles on surface of a semiconductor wafer having repetitive patterns.

Referring now to the drawings, there is illustrated in FIG. 1 an apparatus 11 for use in detecting the presence of particles and/or pattern defects on the front surface 12 surface of a semiconductor wafer 13 having repetitive patterns.

Apparatus 11 includes a holder 15 for holding wafer 13. Holder 15 is mounted on a stage 17 which is movable in two mutually perpendicular directions by a pair of motors 19 and 20, the particular details of the mechanical arrangement for moving stage 17 not being a part of this invention.

Apparatus 11 also includes a light source 21, a Fourier mask 23 which is programmable, a first camera 25 and a second camera 27.

Light source 21 generates a high intensity, plane polarized, coherent, monochromatic beam of light and may be, for example, a ND:YAG laser or a helium-neon laser. In FIG. 1, the beam of light from light source 21 is P polarized relative to wafer 13 and the optics are arranged accordingly.

Fourier mask 23 includes an optically addressable spatial light modulator (SLM) 29. Fourier mask 23 also includes a polarization discriminator in the form of a polarizing beamsplitter 31.

Figure 2:
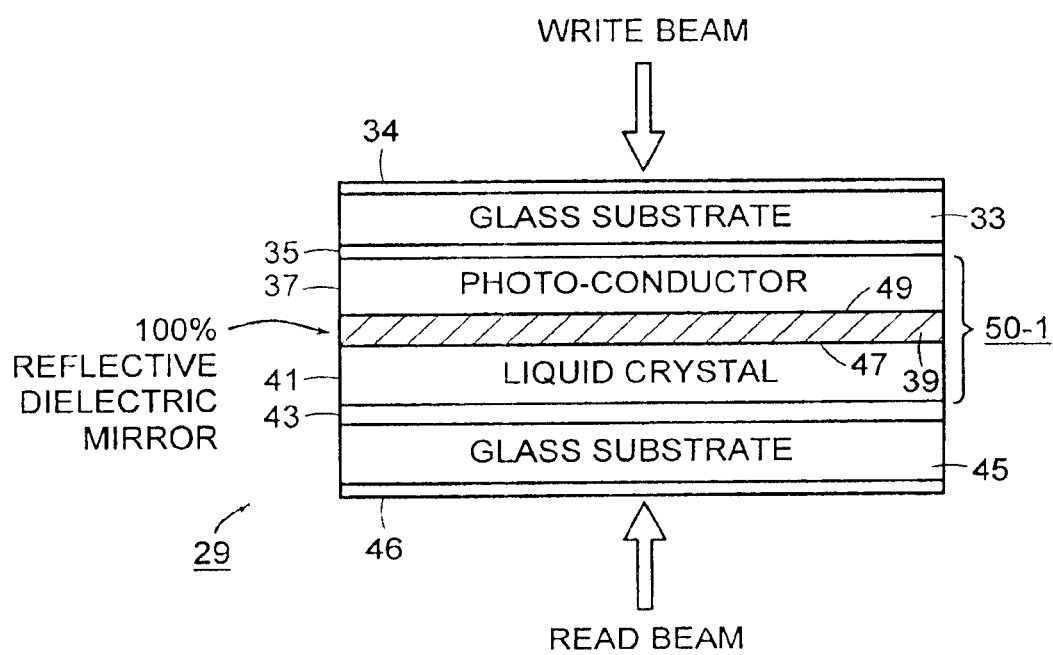
FIG. 2 is a detailed view of the spatial light modulator shown in FIG. 1.

Spatial light modulator 29, which is shown in detail in FIG. 2 includes a back plate of glass 33, an anti-reflection coating 34 on the back side of glass plate 33, a first transparent electrode 35 coated on the front side of glass plate 33, a photoconductive layer 37, such as amorphous silicon, in front of first transparent electrode 35, a 100% reflective dielectric mirror 39 in front of photoconductor 37, a liquid crystal 41 in front of dielectric mirror 39, a second transparent electrode 43 in front of liquid crystal 41, electrode 43 being coated on the back of a plate of glass 45 and an anti-reflection coating 46 on the front side of glass 45.

Dielectric mirror 39 includes a front side 47 and a rear side 49. The thicknesses of layers 33, 37, 39 41 and 45 may be as follows: layers 33 about 5 mm, layer 37 about 3 microns, layer 39 about 1 micron, layer 41 about 1 micron and layer 45 about 5 mm. For simplicity, layers 37, 39 and 41 on spatial light modulator 29 are shown in FIG. 1 as a single line 50-1. Electrodes 35 and 43 are on the order of about 1 micron thick.

SLM 29 is driven by a voltage source 50-2 which may be about 5 volts and which is connected to electrodes 35 and 43.

Optically addressable spatial light modulator 29 may be as an example, a ferroelectric liquid crystal spatial light modulator (FLC-SLM) model number Z4601 made by Hamamatsu Photonics K.K., Central Research Laboratory, Hamakita City, Japan.

First camera 25, which serves as an inspection camera, is a high sensitivity video camera and second camera 27 which serves as s Fourier imaging camera, is a standard video camera. Each camera may be, for example, CCD type cameras.

Apparatus 11 also includes a first imaging lens 51, a second imaging lens 53, a third imaging lens 55, a flat mirror 57, a processor 59 and a liquid crystal display (LCD) 61.

In the operation of apparatus 11, light from source 21 is directed onto front surface 12 of semiconductor wafer 13. Light source 21 is arranged so as to strike surface 12 at an angle $\alpha$ between around 0 and 45 degrees relative to wafer 13. Light scattered upward from the area on surface 12 which is illuminated by the beam of light from source 21 is collected by first imaging lens 51. As can be appreciated, the scattered light collected by first imaging lens 51 includes light scattered from any particles and/or pattern defects which may be present on the area of surface 12 illuminated and, in addition, light scattered from the features of the pattern on the area of the surface illuminated.

A Fourier diffraction pattern of the scattered light collected by first lens 51 and reflected off polarizing beamsplitter 31 is formed at the back focal plane 63 of lens 51. At the same time, scattered light collected by first lens 51 and transmitted through polarizing beamsplitter 31 strikes dielectric mirror 39 in SLM 29, dielectric mirror 39 being disposed also at the back focal plane of lens 51. As will herein be explained, in Fourier mask 23, light whose intensity is above a predetermined intensity level and corresponding to features on the surface of wafer 13 is blocked out.

Light corresponding to the Fourier diffraction pattern formed at back focal plane 63 of lens 51 is deflected off flat mirror 57 and then imaged by second imaging lens 53 onto camera 27. Flat mirror 57 is disposed between second imaging lens 53 and back focal plane 63 and is used to bend the beam of light from back focal plane 63 so as to make apparatus 11 more compact. Second camera 27 converts the video image of the diffraction pattern formed therein into a stream of digital electrical signals. The stream of digital electrical signals from second camera 27 is processed in processor 59, as maybe desired. The processing may include raising the overall gain of the image and/or blocking out selected areas and/or changing the magnitude of the image and/or adjusting the offset of the two images to zero. The output of processor 59 is fed into LCD 61 which converts the digital electrical signals into a video image. The video image formed by LCD 61 is imaged by third imaging lens 55 onto photoconductive layer 37 in SLM 29. The beam of light striking mirror 47 from lens 51 and transmitted through beamsplitter 63 constitutes a "read" beam while the beam of light from LCD 61 and lens 55 striking photoconductor 37 constitutes a "write" beam. The write beam and read beam are axially aligned on their corresponding sides of mirror 39 and adjusted as needed in processor 59. Thus there is point to point correspondence of the write and read beams at spatial light modulator 39.

SLM 29 is configured and oriented to act as a spatially-addressable, variable polarization rotator. (In this specific case, SLM 29 is optically-addressable; i.e. it is spatially addressable via the position of the write beam. The voltage locally applied across liquid crystal layer 41 in SLM 29 is proportional to the intensity of the write beam at that location via photoconductor layer 37.) If SLM 29, for example, incorporates a twisted-nematic liquid crystal, then SLM 29 is oriented such that the optical axis of the crystal's input face is aligned parallel to the input beams's polarization. As previously mentioned, the beam is p-polarized with respect to wafer 13 in FIG. 1. If, on the other hand for example, SLM 29 utilizes a parallel-aligned nematic liquid crystal, then it must be aligned such that its optical axis (in the absence of any applied voltage) makes an angle of 45 degrees with respect to the input beams's polarization. In either case, the configuration is such that the beam undergoes a 90 degree a rotation in polarization in the absence of an applied voltage (weak write beam) and remains unchanged in the presence of a critical applied voltage level (strong write beam).

The diffraction pattern formed by repetitive features on wafer 13 is relatively much stronger than that from a particle or defect. The strong diffraction pattern can therefore be made to activate (via post-processing gain adjustment if necessary) photoconductor layer 57 in those locations. It would thereby undo the rotation of the corresponding diffraction components in the read beam. The weaker diffraction component in the write beam, associated with the particle or defect, would not be of sufficient intensity to active the photoconductor. As such, this would means that particle/defect component in the read beam would have its polarization rotated by 90 degrees upon reflection in the SLM 29. It is this difference in polarization that allows one to optically discriminate between the features and particle/defects on wafer 13.

In those areas (locations) where the intensity of the write beam is below a predetermined threshold level indicative of possible particle and/or pattern defect information, the polarization of the corresponding areas on the read beam on reflection from mirror 39 will be rotated 90 degrees. On the other hand, in those areas where the write beam is above the preselected threshold level indicative of background information, the polarization of corresponding areas on the read beam on reflection from mirror 39 will remain the same; i.e. will not be rotated.

Light reflected from mirror 39 in SLM 29 where the polarization has been rotated is reflected off polarizing beamsplitter 31 and is then imaged onto first camera 25. Light reflected from mirror 39 whose polarization is unchanged is transmitted through beamsplitter 31 and thus does not reach camera 25.

Thus, first 25 camera records an image of light scattered from surface 12 whose intensity is below the predetermined threshold level and caused by particles and/or pattern defects and not scattered light whose intensity is above the threshold level and caused by features.

Wafer 13 is then moved translationally so that other areas on surface 12 may be examined, in a similar manner, one at a time.

As can be appreciated, Fourier mask 23 is programmable in that it automatically blocks out more intense portions of the light in the Fourier diffraction pattern.

Figure 3:
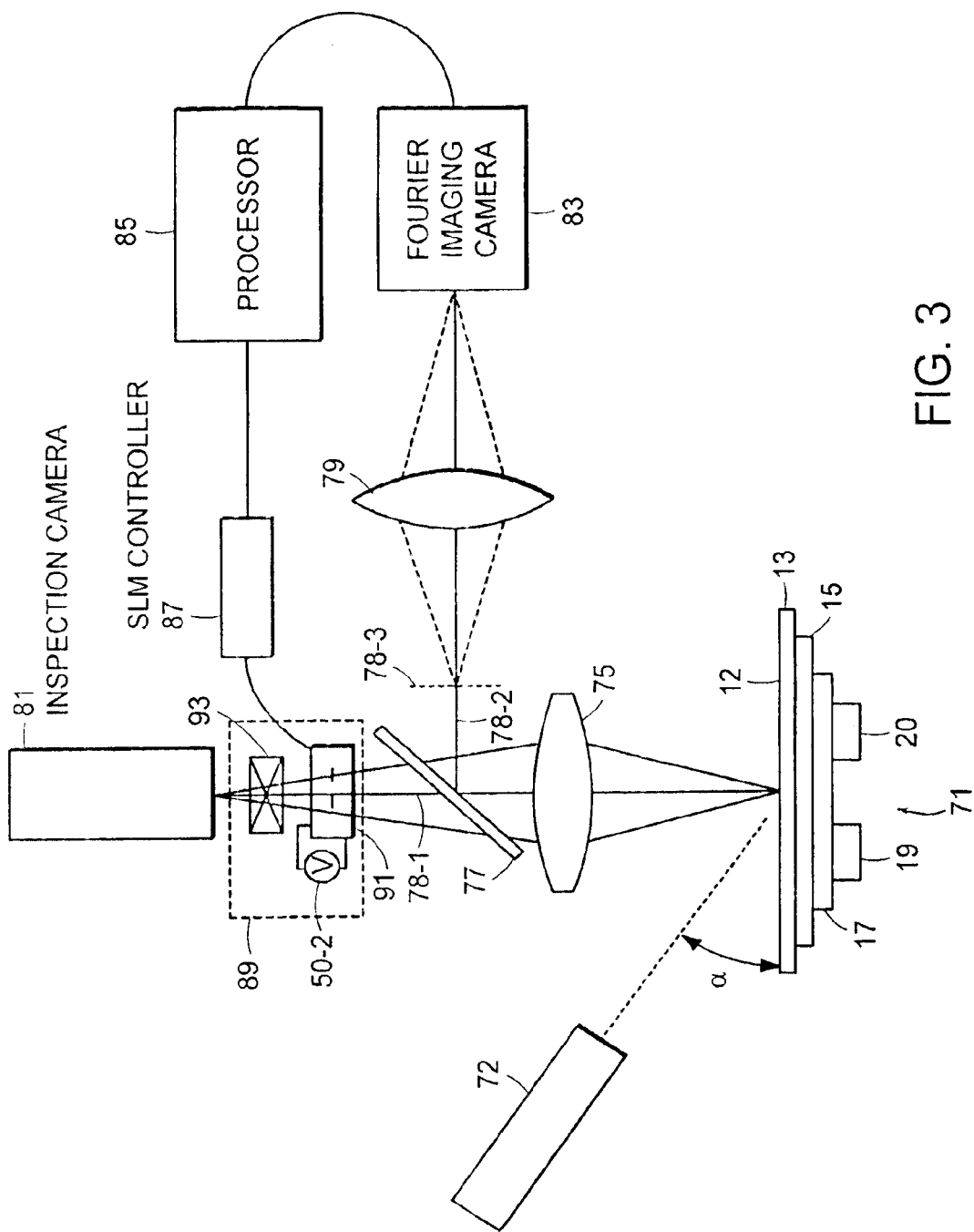
FIG. 3 is a schematic representation of another embodiment of the invention.

Referring now to FIG. 3 there is shown another embodiment of an apparatus constructed according to this invention for detecting the presence of particles and/or pattern defects on the front surface 12 of a semiconductor wafer 13 having repetitive patterns, the apparatus being identified by reference numeral 71. As will hereinafter be explained in more detail, apparatus 1 includes an electrically addressable SLM rather than an optically addressable SLM as in apparatus 11.

Figure 4:
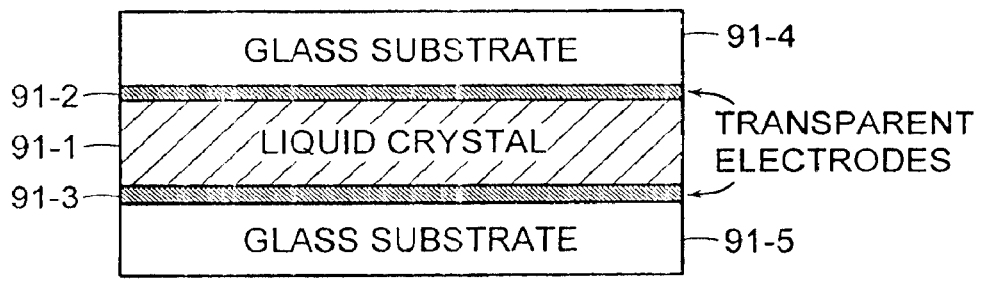
FIG. 4 is a detailed view of the spatial light modulator shown in FIG. 3.

Apparatus 71 includes a light source 72, a first imaging lens 75, a beamsplitter 77, a second imaging lens 79, a first camera 81, a second camera 83, a processor 85, an SLM controller 87, and a Fourier mask 89, Fourier mask 89 comprising an electrically addressable SLM 91 arranged for operation in a transmissive mode and a crossed polarizer 93. Light source 72, first camera 81 and second camera 83 correspond structurally and functionally to light source 21, first camera 25 and second camera 27, respectively. SLM 91 is shown in detail in FIG. 4 and includes a liquid crystal layer 91-1, a pair of transparent electrodes 91-2 and 91-3 and a pair of glass substrates 91-4 and 91-5. Apparatus also includes apparatus 71 includes a holder 15 for holding wafer 13. Holder 15 is mounted on a stage 17 which is movable in two mutually perpendicular directions by a pair of motors 19 and 20, the particular details of the mechanical arrangement for moving stage 17 not being a part of this invention.

The beam of light from laser 72 is arranged to strike wafer 13 at an angle α of about 0 to 40 degrees. In the operation of apparatus 71, SLM 91 is configures and oriented to act as a spatially-addressable, variable polarization orator. (In this specific case, the SLM is electrically addressable; i.e. it is spatially addressable via the direct application of voltage to specific x, y pads in the transparent electrodes.) If SLM 91, for example, incorporates a twisted-nematic liquid crystal, then the SLM is to be oriented such that the optical axis of the crystal's input face is aligned parallel to the input beam's polarization. As previously mentioned, the beam is p-polarized with respect to the wafer in FIG. 3. If, on the other hand for example, SLM 91 utilizes a parallel-aligned nematic liquid crystal, then it must be aligned such that its optical axis (in the absence of any applied voltage) makes an angle of 45 degrees with respect to the input beam's polarization. In either case, the configuration is such that the beam undergoes a 90 degree rotation in polarization in the absence of an applied voltage and remains unchanged in the presence of a critical applied voltage level. The applied voltage is directly proportional to the processed diffraction image from camera 83. The more intense the signal (i.e. strong diffraction from repetitive features on the wafer) the higher will be the applied voltage to undo the polarization rotation of the corresponding components of beam 78-1 which would then be blocked by the cross-polarizer 89. The less intense signal (i.e. weak diffraction from particles and or defects on the wafer), the lower will be the applied voltage to liquid crystal layer 91-1. This would result in a 90 degree polarization rotation of the weaker components of beam 78-1; this would then pass through the crossed-polarizer to camera 81. Signal discrimination between unwanted features on the wafer and desirable defects/particulates would thus be possible.

Light scattered upward from the area illuminated is collected by first imaging lens 75 and strikes beamsplitter 77 where it is split into a transmitted beam 78-1 and a reflected beam 78-2. A Fourier transformation of the light collected by first imaging lens using light from the reflected beam 78-2 is formed at the back focal plane 78-3 of first lens 75. At the same time, light collected by first lens 75 that is transmitted through beamsplitter 77 strikes Fourier mask 89. The area illuminated is then imaged onto first camera 81 using scattered light that is not blocked out by Fourier mask 89.

Second imaging lens 79 images the Fourier transformation formed at Fourier plane 78-3 onto second camera 83 where the image is converted into a stream of digital electrical signals. The stream of digital electrical signals from camera 83 is processed in processor 85, as maybe desired. The processing may include raising the overall gain of the image, or making the offset between the two images zero, or blocking out selected areas or changing the magnitude of the image so as to correspond in size exactly to the image transmitted through beamsplitter 77 and striking SLM 91. Controller 87 applies voltage signals to electrically addressable SLM 91 in accordance with information it receives from processor 85.

Fourier mask 89 operates in the following manner. In the absence of any externally applied voltage, the polarization of the light is rotated by 90 degrees and thereby passes through crossed polarizer 89 to inspection camera 81. In the presence of a sufficiently intense applied voltage, SLM 91 ceases to function as a polarization rotator. In that case the light gets r, blocked by crossed polarizer 89.

Figure 5:
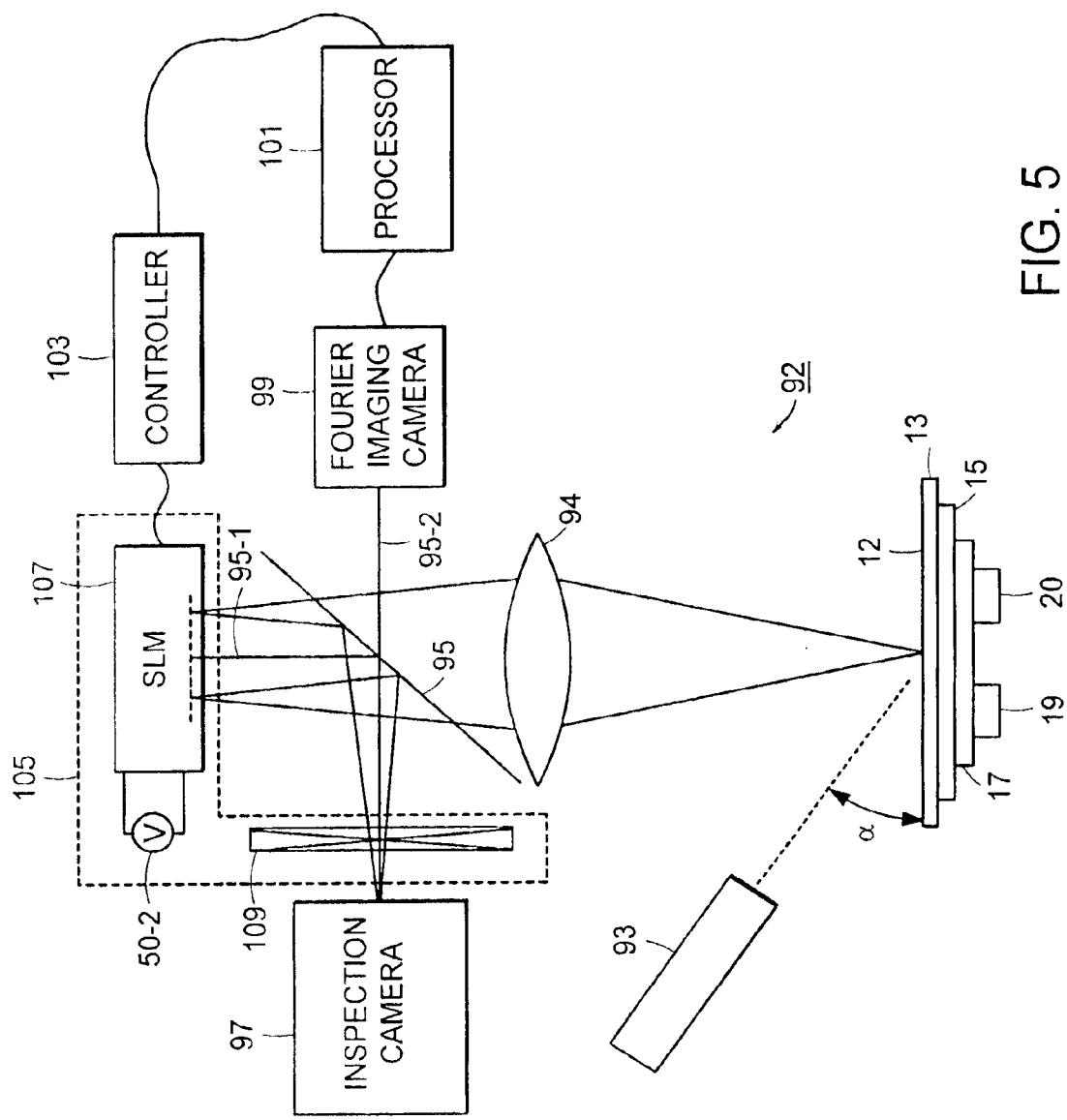
FIG. 5 is a schematic representation of another embodiment of the invention.

Referring now to FIG. 5 there is shown another embodiment of an apparatus constructed according to this invention, the apparatus being identified by reference numeral 92. As will hereinafter be explained in more detail, apparatus 92 is somewhat similar to apparatus 71 in that it includes an electrically addressable SLM rather than an optically addressable SLM as in apparatus 11. However, SLM in this embodiment operates in a reflective mode rather than in a transmissive mode as in the FIG. 3 embodiment.

Apparatus 92 includes a light source 93, a first imaging lens 94, a beamsplitter 95, a first camera 97, a second camera 99, a processor 101, an SLM controller 103, and a Fourier mask 105 comprising an electrically addressable SLM 107 arranged for operation in a reflective mode and a crossed polarizer 109. Apparatus 92 also includes a holder 15 for holding water 13. Holder 15 is mounted on a stage 17 which is movable in two mutually perpendicular directions by a pair of motors 19 and 20, the particular details of the mechanical arrangement for moving stage 17 not being a part of this invention.

Figure 6:
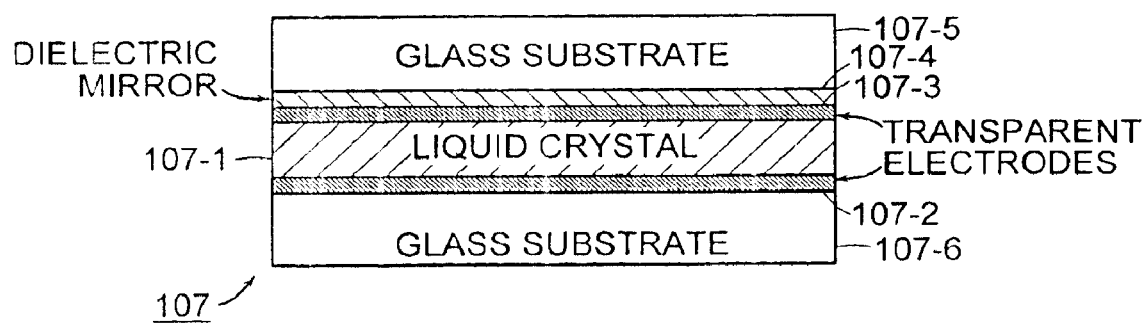
FIG. 6 is a detailed view of the spatial light modulator shown in FIG. 5.

Light source 93, first imaging lens 94, first camera 97 and second camera 99 correspond functionally and structurally to light source 21, first imaging lens 51, first camera 25 and second camera 27, respectively. SLM 107 is shown in detail in FIG. 6 and includes a liquid crystal 107-1, a pair of transparent electrodes 107-2 and 1-7-3, a dielectric mirror 107-4 and a pair of glass substrates 107-5 and 107-6.

In the operation of apparatus 92, light from source 93 strikes surface 12 of wafer 13 at an angle of incidence a which is preferably between 0 and 45 degrees.

Light scattered upward from the area illuminated is collected by first imaging lens 94 and strikes beamsplitter 95 where it is split into a transmitted beam 95-1 and a reflected beam 95-2. A Fourier transformation of the light collected by first imaging lens 94 using light from the reflected beam 95-2 is formed is formed at second camera 99. At the same time, light collected by first lens 94 that is transmitted through beamsplitter strikes SLM 107 whose liquid crystal is in the back focal plane of lens 93.

The Fourier transformation formed at second camera 99 is converted into a stream of digital electrical signals. The stream of digital electrical signals from camera 99 is processed in processor 101, as maybe desired. The processing may include raising the overall gain of the image, or blocking out selected areas or changing the magnitude of the image so as to correspond in size exactly to the image transmitted through beamsplitter 95 and striking SLM 107. Controller 103 applies voltage signals to electrically addressable SLM 107 in accordance with information it receives from processor 101.

Fourier mask 105 operates in the following manner. In the absence of any externally applied voltage, SLM 107 is configured and oriented such that the polarization of the light striking SLM 107 is rotated by 90 degrees and on reflection from SLM 107 is reflected off beamsplitter 95 and passes through crossed polarizer 109 to first camera 91. In the presence of a sufficiently intense applied voltage, SLM 107 ceases to function as a polarization rotator. In that case the reflected light gets blocked by crossed polarizer 109. Thus, an image of the area illuminated by light source 93 is formed on camera 97 using scattered light that is not blocked out by Fourier mask 105.

Figure 7:
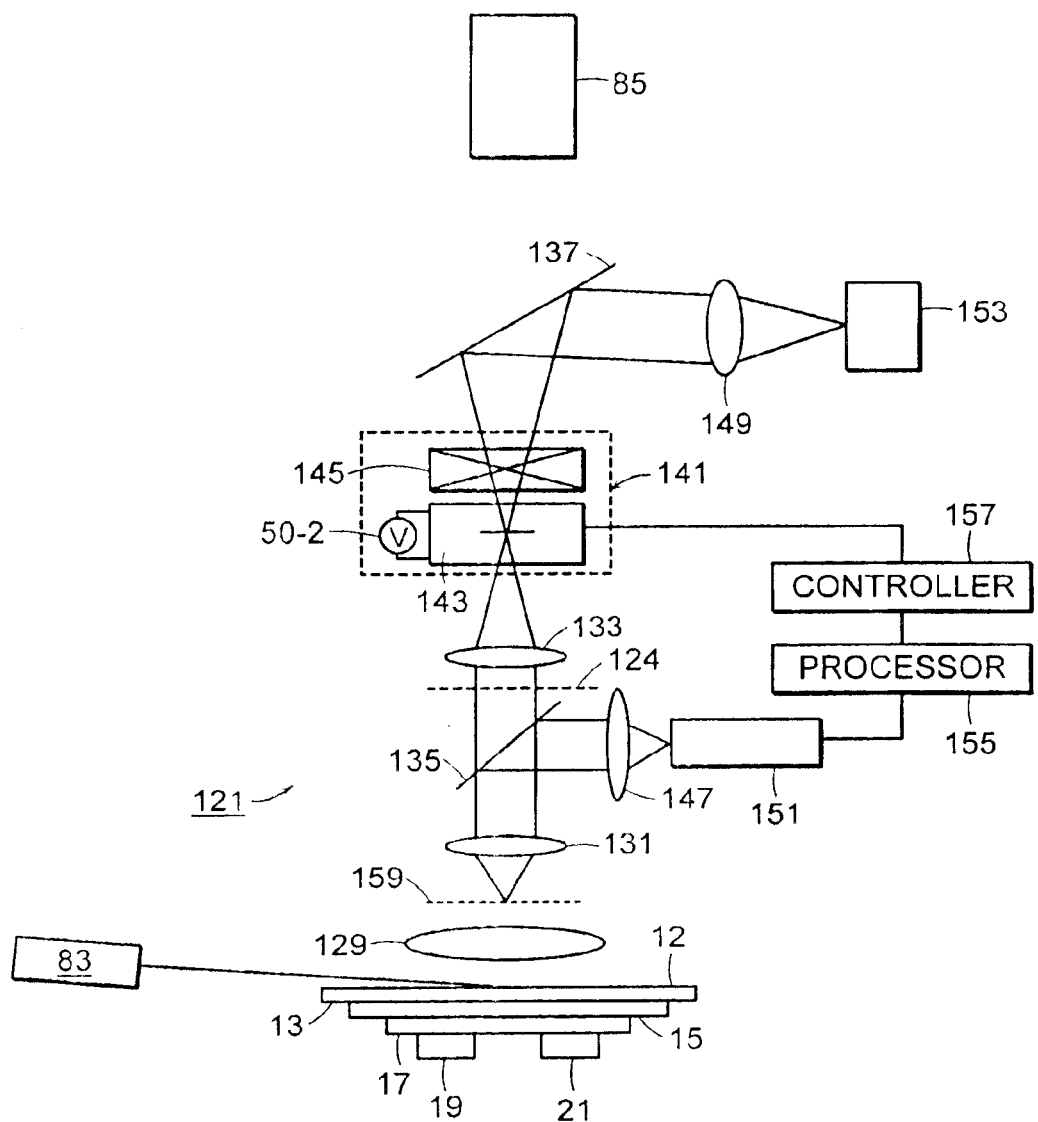
FIG. 7 is a schematic representation of another embodiment of the invention.

Referring now to FIG. 7 there is shown another embodiment of an apparatus constructed according to this invention, the apparatus being identified by reference numeral 121.

Apparatus 121 includes a light source 83, a first light camera 85, a first lens 129, a second lens 131, a third lens 133, a first beamsplitter 135 and a second beamsplitter 137.

Apparatus 121 also includes a programmable Fourier mask 141, having an electrically addressable SLM 143 identical to SLM 91 and a crossed polarizer 145, a sixth lens 147, a seventh lens 149, a second camera 151, a third camera 153, a processor 155 and an SLM controller 157. Camera 85, 151 and 153 may be CCD cameras.

Lens 147 in combination with lens 131 images the Fourier diffraction pattern formed in Fourier plane 159 of lens 129 into camera 151 where the image is converted into a stream of digital electrical signals. The stream of digital electrical signals are processed in processor 155, as maybe desired. The processing may include raising the overall gain and/or magnitude of the image and/or blocking out selected areas and/or making the offset of the two images zero. The output of processor 155 is fed into controller 157. The output of controller 157 is fed into SLM 143. At the same time, lens 131 in combination with lens 133 images the Fourier diffraction pattern formed at Fourier plane 159 onto the liquid crystal in SLM 143. Lens 129 in combination with lens 131 forms an image of the area illuminated by light source 123 at image plane 124. The image formed at image plane 124 is then collected by lens 133 is passed through Fourier mask 141. The filtered image is then transmitted through beamsplitter 139 and then brought to focus at first camera 85. The refraction pattern at Fourier plane 159 is imaged by lenses 149, 131 and 133 onto camera 153 so that the alignment of the two images on SLM 143 can be viewed.

Figure 8:
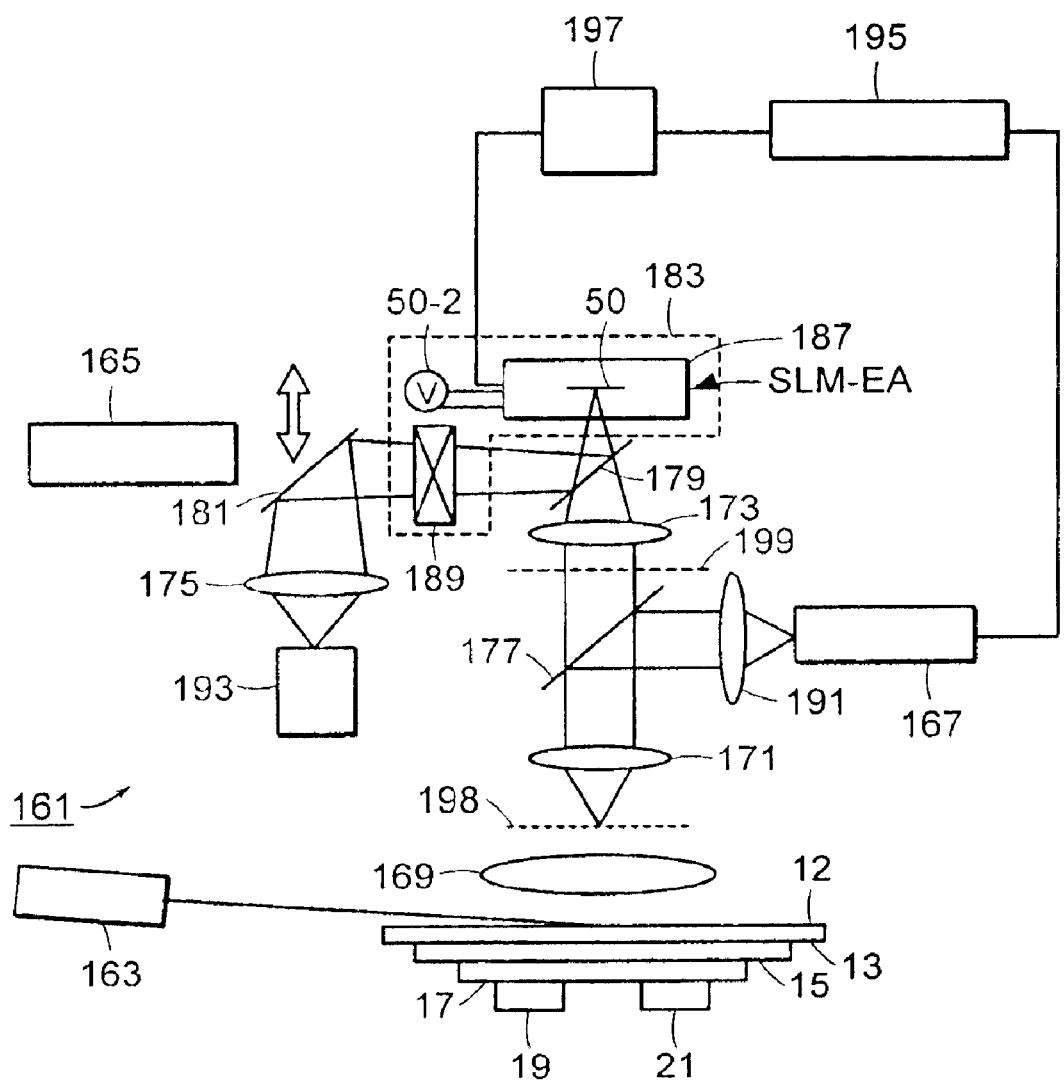
FIG. 8 is a schematic representation of another embodiment of the invention.

Referring now to FIG. 8 there is shown another embodiment of an apparatus constructed according to this invention, the apparatus being identified by reference numeral 161.

Apparatus 161 includes a light source 163, a first camera 165, a second camera 167, a first lens 169, a second lens 171, a third lens 173, a fourth lens 175, a first beamsplitter 177, a second beamsplitter 179 and a third beamsplitter 181.

Apparatus 161 also includes a programmable Fourier mask 183 having an electrically addressable SLM 187 identical to SLM 107 and a crossed polarizer 189, a fifth lens 191, a third camera 193, a processor 195 and an SLM controller 197.

Lens 191 in combination with lens 171 images the Fourier diffraction pattern formed in Fourier plane 198 of lens 169 into camera 167 where the image is converted into a stream of digital electrical signals. The stream of digital electrical signals is processed in processor 195, as maybe desired. The processing may include raising the overall gain and/or adjusting the offset to assure zero offset and/or adjusting the magnitude of the image or blocking out selected areas. The output of processor 195 is fed into controller 197 whose output is fed into SLM 187. At the same time, lens 171 in combination with lens 169 forms an image of the area illuminated by light source 83 at image plane 199. The image formed at image plane 199 is then collected by lens 173 and strikes SLM 187 through beamsplitter 179. The image reflected off the liquid crystal in SLM 187 is reflected off beamsplitter 179, then passed through crossed polarizer 189 and then imaged onto camera 165. Liquid crystal plane in SLM 187 is imaged by lens 175 onto camera 193 after it is reflected by beamsplitter 179, passed through crosspolarizer 189 and reflected by mirror 181 for the purpose of viewing image alignment.

The embodiments of the present invention recited herein are intended to be merely exemplary and those skilled in the art will be able to make numerous variations and modifications to it without departing from the spirit of the present invention. For example, an array of photodiodes can be used in place of any or each one of the cameras. Also, if the laser beam is S polarized rather than P polarized, the polarization sensitive optics would have to be adjusted accordingly. Also, the laser beams could be oriented at an angle α greater than 45 degrees if desired, even as high as 90 degrees, in which case the detection would be in bright field. All such variations and modifications are intended to be within the scope of the present invention as defined by the claims appended hereto.

What is claimed is:

1. Apparatus for detecting particles on a surface of a semiconductor wafer, said surface having repetitive patterns, the apparatus comprising:
   (a) a laser for illuminating an area on said surface with a beam of polarized light,
   (b) a first camera,
   (c) a first imaging lens for collecting light scattered from said area, said first imaging lens forming a Fourier diffraction pattern of light scattered from said area illuminated at the back focal plane of said first imaging lens,
   (d) a Fourier mask for blocking light in said Fourier diffraction pattern where the intensity is above a predetermined level indicative of of background information and leaving in areas where the intensity is below said predetermined level indicative of particle information, the Fourier mask including a spatial light modulator (SLM) which is optically addressable and a polarization discriminator in the form of a polarizing beamsplitter, the polarizing beamsplitter being disposed optically between the first imaging lens and the SLM the SLM including a 100% reflective dielectric mirror and a photoconductive layer, the polarizing beamsplitter receiving light collected by said first imaging lens and splitting said light so collected into a transmitted beam and a reflected beam, the first camera being disposed along the path of the transmitted beam,
   (e) a second camera disposed along the path of the reflected beams,
   (f) a second imaging lens for imaging the Fourier diffraction pattern formed by the first imaging lens of light from the reflected beam in the back focal plane of the first imaging lens into the second camera, said second camera converting the image of the Fourier diffraction patterns into a stream of digital electrical signals,
   (g) light from the polarizing beamsplitter in the transmitted beam striking the 100% reflective dielectric mirror which is disposed in the back focal plane of the first imaging lens,
   (h) a processor for processing the stream of digital electrical signals formed by the second camera,
   (i) a liquid crystal display (LCD) for converting the output of the processor into a video image, and
   (j) a third imaging lens for imaging the video image of the LCD onto the photoconductive layer in the SLM,
   (k) light reflected back from said 100% reflective dielectric mirror as modified by light striking the photoconductive layer from the LCD is reflected by said polarizing beamsplitter and imaged onto said first camera, said first camera recording the image of the area imaged by said first imaging lens using scattered light not blocked by said Fourier mask.

2. Apparatus for detecting particles on a surface of a semiconductor, said surface having repetitive patterns, the apparatus comprising:
   (a) a laser for illuminating an area on said surface with a beam of polarized light,
   (b) a first imaging lens for collecting light scattered from said area, said first imaging lens forming a Fourier diffraction pattern of light scattered from the area at the back local plane of the first imaging lens,
   (c) a beamsplitter disposed optically behind the first imaging lens for splitting the light collected by the first imaging lens into a transmitted beam and a reflected beam,
   (d) a first camera disposed along the path of the transmitted beam at the image plane of the first imaging lens,
   (e) a Fourier mask disposed between the beamsplitter and the first camera, the Fourier mask including an electrically addressable spatial light modulator (SLM) operating in a reflective mode and a crossed polarizer, said SLM being disposed optically behind said beamsplitter in the Fourier transform plane of light from the first imaging lens in the transmitted beam, said Fourier mask blocking off light in said diffraction pattern where the intensity is above a predetermined level indicative of background information and leaving reflecting light in areas back to said beamsplitter where the intensity is below said predetermined level indicative of particle information, said crossed polarizer being disposed optically between said SLM and said first camera,
   (f) a second camera disposed along the back focal plane of the first imaging lens for converting an image of the diffraction pattern formed by the first imaging lens using light in the reflected beam from the beamsplitter into a stream of digital electrical signals,
   (g) a processor for processing the stream of digital electrical signals formed by the second camera, and
   (h) an SLM controller for applying the output of the processor into the SLM,
   (i) light striking the SLM from the transmitted beam, reflected back from said SLM and then reflected by said beamsplitter and not blocked by said crossed polarizer is imaged onto said first camera, said first camera recording an image of the area illuminated by said first imaging lens and not blocked by said Fourier mask.

* * * * *